(12) United States Patent
Kondo et al.

(10) Patent No.: US 11,213,227 B2
(45) Date of Patent: Jan. 4, 2022

(54) PULSE OXIMETER

(71) Applicant: Murata Vios, Inc., Woodbury, MN (US)

(72) Inventors: Nobuhiro Kondo, Woodbury, MN (US); Yoshitaka Hane, Nagaokakyo (JP); Kenichi Fukuda, Nagaokakyo (JP); Masamichi Yanai, Woodbury, MN (US)

(73) Assignee: MURATA VIOS, INC., Woodbury, MN (US)

( * ) Notice: Subject to any disclaimer, the term of this patent is extended or adjusted under 35 U.S.C. 154(b) by 113 days.

(21) Appl. No.: 16/856,586

(22) Filed: Apr. 23, 2020

(65) Prior Publication Data

US 2021/0330222 A1     Oct. 28, 2021

(51) Int. Cl.
*A61B 5/1455*     (2006.01)
*A61B 5/00*     (2006.01)

(52) U.S. Cl.
CPC ........ *A61B 5/14552* (2013.01); *A61B 5/6826* (2013.01); *A61B 5/6838* (2013.01); *A61B 2562/164* (2013.01)

(58) Field of Classification Search
CPC .............. A61B 5/1455; A61B 5/14551; A61B 5/14552; A61B 5/6826; A61B 5/6838; A61B 2562/0233; A61B 2562/164
See application file for complete search history.

(56) References Cited

U.S. PATENT DOCUMENTS

| | | | | |
|---|---|---|---|---|
| 6,461,305 B1 * | 10/2002 | Schnall | ................ | A61B 5/6826 600/342 |
| 6,801,798 B2 * | 10/2004 | Geddes | ................ | A61B 5/6826 600/323 |
| 7,650,177 B2 * | 1/2010 | Hoarau | ................ | A61B 5/6826 600/344 |
| 7,742,794 B2 * | 6/2010 | Todokoro | ............. | A61B 5/6826 600/344 |
| 8,260,391 B2 * | 9/2012 | Hoarau | ................ | A61B 5/6826 600/344 |
| 2005/0075550 A1 | 4/2005 | Lindekugel | | |
| 2014/0005557 A1 * | 1/2014 | Rich | ................ | A61B 5/14552 600/479 |

* cited by examiner

*Primary Examiner* — Eric F Winakur
(74) *Attorney, Agent, or Firm* — Keating & Bennett, LLP

(57) ABSTRACT

A pulse oximeter includes a curved holder. A flexible substrate is coupled to a curved inner surface of an outer portion of the curved holder. A light emitter, a light receiver, and a reinforcement are coupled to a curved inner surface of the flexible substrate. The reinforcement is curved to extend in conformance with the curved form of the flexible substrate. The material of the reinforcement has a Young's modulus that is larger than the Young's modulus of the material of the outer portion and the Young's modulus of the material of an inner portion.

6 Claims, 2 Drawing Sheets

PULSE OXIMETER

BACKGROUND OF THE INVENTION

1. Field of the Invention

The present disclosure relates to a pulse oximeter.

2. Description of the Related Art

U.S. 2005/0075550 A1 describes a pulse oximeter for measuring the blood oxygen saturation level and pulse. The pulse oximeter includes a holder attached to a finger of a user. The holder is shaped to clamp the finger of the user. A light emitter and a light receiver are coupled to the holder. In the pulse oximeter, light is projected toward the finger from the light emitter, and a change in the amount of light passing through the finger is obtained to measure the blood oxygen saturation level and pulse.

SUMMARY OF THE INVENTION

In a pulse oximeter such as that described in US 2005/0075550 A1, the holder is typically formed from a soft material such as rubber or synthetic resin in view of the feel of the holder. However, when using a soft material as the material of the holder, the force clamping the finger of the user may be weak. Thus, when the holder is attached to the finger of the user, the holder may fall off from the finger.

A preferred embodiment of the present invention provides a pulse oximeter including a holder, a light emitter coupled to the holder to emit light inwardly from the holder, a light receiver arranged at a position opposed to the light emitter to receive the light emitted from the light emitter, and a reinforcement arranged inside the holder that extends from the light emitter to the light receiver in conformance with the curved form of the holder, and a material of the reinforcement has a Young's modulus that is greater than a Young's modulus of a material of the holder.

In the configuration described above, the Young's modulus of the material of the reinforcement is greater than the Young's modulus of the material of the holder. Thus, even when a soft material is used as the material of the holder, the reinforcement acts to appropriately increase the flexural rigidity of the pulse oximeter in its entirety. Accordingly, when the holder is attached to the finger, the holder is easily kept on the finger.

The holder of the pulse oximeter is easily kept on the finger.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Preferred embodiments of pulse oximeters will now be described with reference to the drawings.

Figure 1:
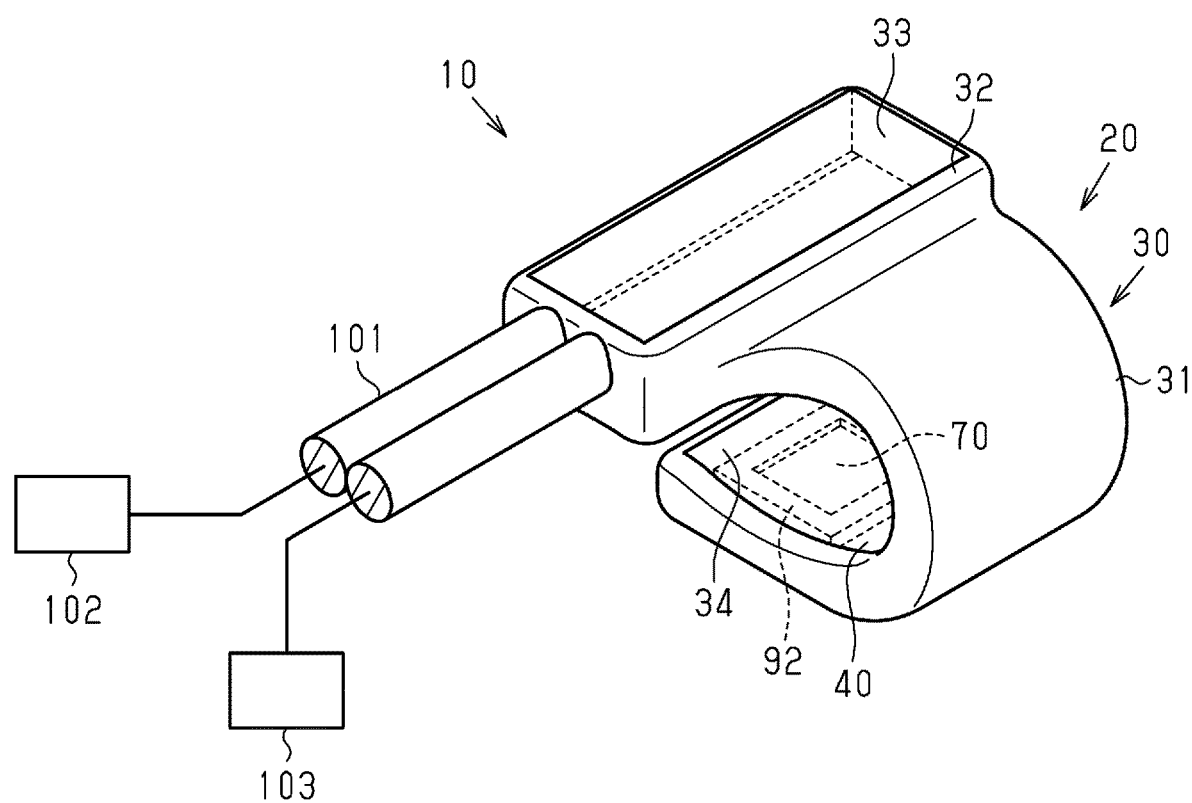
FIG. 1 is a perspective view of a pulse oximeter.
Figure 2:
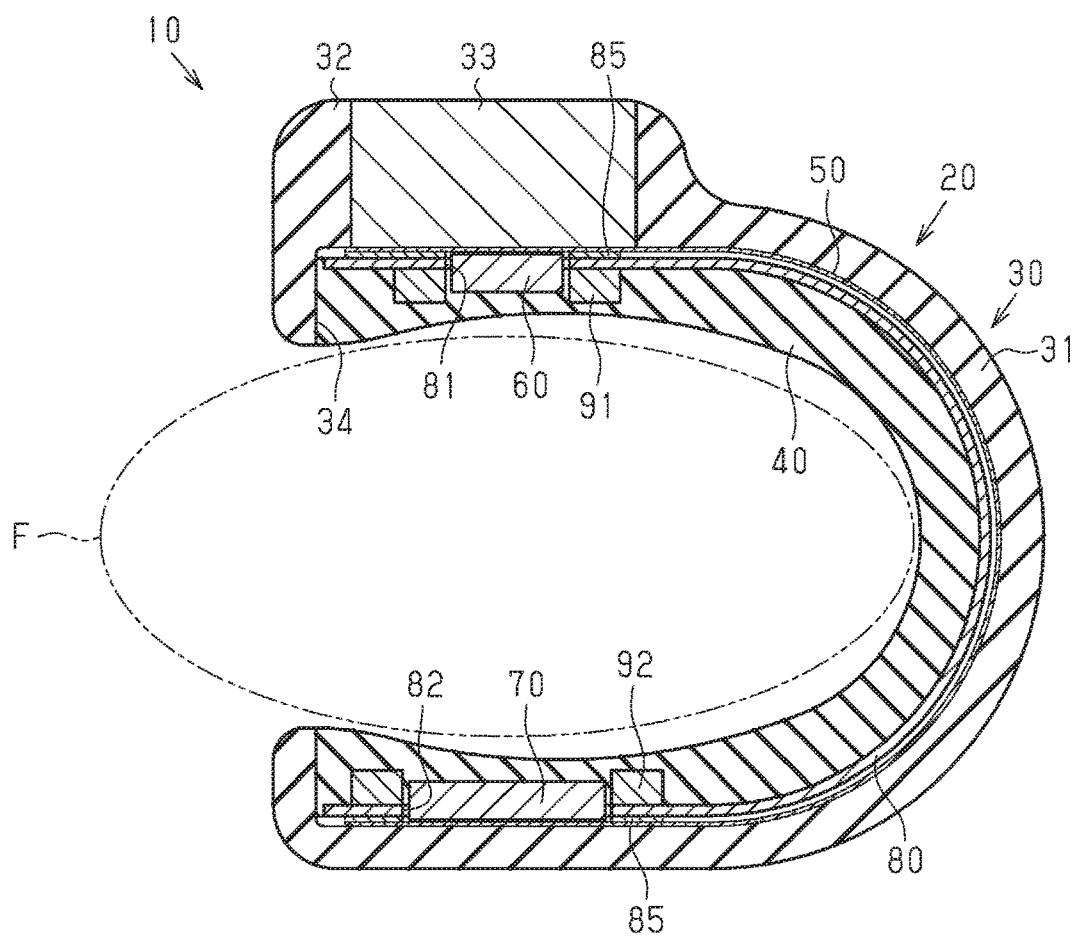
FIG. 2 is a cross-sectional view of the pulse oximeter.

As shown in FIG. 1, a pulse oximeter 10 includes a holder 20 preferably with a curved band plate form so that the two longitudinal ends of the holder 20 are located near each other. The two ends of the holder are separated and not connected to each other. More specifically, as shown in FIG. 2, the holder 20 is substantially C-shaped in a cross-sectional view and curved by approximately 180 degrees so that the two longitudinal ends are directed in the same direction.

The exterior of the curved holder 20 is formed by an outer portion 30. The material of the outer portion 30 is silicone rubber that has a Shore A hardness of 70. The color of the outer portion 30 under visible light is black. Further, the outer portion 30 absorbs infrared light and limits the transmission of infrared light. The Shore A hardness is obtained with a durometer that presses a cylindrical scale against the surface of the measured material to indent the material and to measure the hardness from the depth of the indentation, which is the pressed depth of the scale.

As shown in FIG. 1, the outer portion 30 includes an outer portion body 31, which has the form of a curved band plate, and a retainer 32, which is connected to one longitudinal end of the outer portion body 31. When a direction that is orthogonal to the longitudinal direction of the outer portion body 31 is defined as the widthwise direction, the retainer 32 has a greater dimension in the widthwise direction than the outer portion body 31. Further, the retainer 32 has a greater thickness than the outer portion body 31. As shown in FIG. 2, the retainer 32 has an inner surface that is smoothly continuous with the inner surface of the outer portion body 31 so that a step is not formed between the inner surfaces. Accordingly, a portion of the retainer 32 projects outward from the outer surface of the outer portion body 31. The outer surface of the retainer 32 is hollowed into a retaining cavity 33. The retaining cavity 33 is box-shaped. The retaining cavity 33 is hollowed over substantially the entire retainer 32.

The curved inner surface of the outer portion 30 is hollowed into a recess 34. The recess 34 extends over substantially the entire outer portion 30 in the longitudinal direction of the outer portion 30 from the retainer 32 to the outer portion body 31. The recess 34 has one longitudinal end connected to the retaining cavity 33 of the retainer 32 in the thickness-wise direction of the outer portion 30. In this preferred embodiment, the recess 34 does not extend to the two longitudinal ends of the outer portion 30. The recess 34 has a dimension in the widthwise direction that is not constant over its entire region in the longitudinal direction.

As shown in FIG. 2, a flexible substrate 50 is coupled to a bottom surface of the recess 34, that is, the curved inner surface of the outer portion 30. The flexible substrate 50 has the form of a band plate. The flexible substrate 50 extends over substantially the entire outer portion 30 in the longitudinal direction of the outer portion 30 from the retainer 32 to the outer portion body 31. Accordingly, the flexible substrate 50 partitions the recess 34 and the retaining cavity 33 at one longitudinal end of the recess 34. The flexible substrate 50 has a thickness that is much smaller than that of the outer portion 30. The flexible substrate 50 has a multilayer structure in which wiring layers are stacked with electrical insulating layers located in between. The flexible substrate 50 has a lower flexural rigidity than the holder 20. Flexural rigidity is the resistance of a member to bending and is determined by the product of the second moment of area of the member and the Young's modulus of the material of the member.

A light emitter 60, which emits light, is coupled to the curved inner surface of the flexible substrate 50. The light emitter 60 is disposed on one longitudinal end of the flexible substrate 50. The light emitter 60 is electrically connected to a wiring layer in the flexible substrate 50. The light emitter 60 emits light inwardly from the curved holder 20. Further, the light emitter 60 emits red light and infrared light.

As shown in FIG. 2, a light receiver 70, which receives the light emitted from the light emitter 60, is coupled to the curved inner surface of the flexible substrate 50. The light receiver 70 is disposed on the other longitudinal end of the flexible substrate 50 at a position opposing the light emitter 60. In the present preferred embodiment, the light receiver 70 is disposed along the axis of the light emitted from the light emitter 60. The light receiver 70 is electrically connected to the wiring layer in the flexible substrate 50.

As shown in FIG. 1, a cable group 101 extends into the retaining cavity 33 of the outer portion 30. Each cable of the cable group 101 is connected to the flexible substrate 50 at a location in the retaining cavity 33 where the flexible substrate 50 is exposed. The light emitter 60 and the light receiver 70 receive electric power, transmit signals, and send signals through the cable group 101 and the flexible substrate 50. The retaining cavity 33 is filled with an electrical insulating resin such as a silicone potting resin or an epoxy resin. As schematically shown in FIG. 1, the other end of the cable group 101 is connected to a power supply 102 and a measurement device 103.

As shown in FIG. 2, a reinforcement 80 is coupled to the curved inner surface of the flexible substrate 50. The reinforcement 80 has the form of a band plate. The reinforcement 80 is curved to extend in conformance with the curved form of the flexible substrate 50. In the present preferred embodiment, the reinforcement 80 functions as a leaf spring. The reinforcement 80 has substantially the same thickness as the flexible substrate 50. The reinforcement 80 has a dimension in the direction of its short side satisfying the required rigidity that it was designed to obtain. In this preferred embodiment, the dimension of the reinforcement 80 in the direction of its short side is substantially the same as that of the flexible substrate 50. The dimension of the reinforcement 80 in the longitudinal direction is substantially the same as that of the flexible substrate 50. The reinforcement 80 includes an emitter receptacle 81 at a location opposed to the light emitter 60. The light emitter 60 is disposed inside the emitter receptacle 81. The light emitter 60 projects from the emitter receptacle 81 into the curved reinforcement 80. Further, the reinforcement 80 includes a receiver receptacle 82 at a location opposed to the light receiver 70. The light receiver 70 is disposed inside the receiver receptacle 82. The light receiver 70 projects from the receiver receptacle 82 into the curved reinforcement 80. The material of the reinforcement 80 is stainless steel.

The reinforcement 80 is adhered by an adhesive layer 85 to the flexible substrate 50. The adhesive layer 85 on the curved inner surface of the flexible substrate 50 extends around the light emitter 60 so as to surround the light emitter 60. Further, the adhesive layer 85 on the curved inner surface of the flexible substrate 50 extends around the light receiver 70 so as to surround the light receiver 70. The flexible substrate 50 is fixed by the adhesive layer 85 to the reinforcement 80.

An emitter light shield wall 91 projects from the curved inner surface of the reinforcement 80. The emitter light shield wall 91 extends along the edge of the emitter receptacle 81. In this preferred embodiment, the emitter light shield wall 91 extends along the entire edge of the emitter receptacle 81. The emitter light shield wall 91 has a distal end located further inward from the end of the light emitter 60 located toward the inner side of the curved flexible substrate 50. As a result, the emitter light shield wall 91 surrounds the outer perimeter of the light emitter 60 in a view of the light emitter 60 taken from the light receiver 70.

A receiver light shield wall 92 projects from the curved inner surface of the reinforcement 80. The receiver light shield wall 92 extends along the edge of the receiver receptacle 82. In this preferred embodiment, the receiver light shield wall 92 extends along the entire edge of the receiver receptacle 82. The receiver light shield wall 92 has a distal end located further inward from the end of the light receiver 70 located toward the inner side of the curved flexible substrate 50. As a result, the receiver light shield wall 92 surrounds the outer perimeter of the light receiver 70 in a view of the light receiver 70 taken from the light emitter 60.

An inner portion 40 is fitted into the recess 34 of the outer portion 30. More specifically, the interior of the curved holder 20 is formed by the inner portion 40. The inner portion 40 has the form of a band plate and is shaped in correspondence with the recess 34. The inner portion 40 covers the reinforcement 80 in addition to the light emitter 60, the light receiver 70, the emitter light shield wall 91, and the receiver light shield wall 92 from the inner side in the curved direction. Thus, the reinforcement 80 is located between the outer portion 30 and the inner portion 40. That is, the reinforcement 80 is arranged inside the holder 20.

From the light emitter 60 to the light receiver 70 in the longitudinal direction of the holder 20, the portion of the holder 20 including the outer portion body 31 has a constant thickness. From the light emitter 60 to the light receiver 70 in the longitudinal direction of the holder 20, the portion of the holder 20 including the outer portion body 31 has a constant width Wd. Thus, from the light emitter 60 to the light receiver 70 in the longitudinal direction of the holder 20, the portion including the outer portion body 31 is where the cross-sectional area is the smallest in a direction orthogonal to the longitudinal direction of the holder 20.

The material of the inner portion 40 is silicone rubber that has a Shore A hardness of 30. Thus, the inner portion 40 is formed from a softer material than the outer portion 30. The inner portion 40 is colorless and transparent under visible light. Further, the inner portion 40 allows for the transmission of a certain amount of infrared light. Accordingly, the inner portion 40 has a higher transmittance than the outer portion 30 with respect to the light emitted from the light emitter 60.

As described above, the material of the reinforcement 80 is stainless steel. Thus, the material of the reinforcement 80 has a Young's modulus that is greater than the Young's modulus of the material of the outer portion 30 and the Young's modulus of the material of the inner portion 40.

The operation of the present preferred embodiment when using the pulse oximeter 10 in accordance with the present preferred embodiment will now be described.

Figure 3:
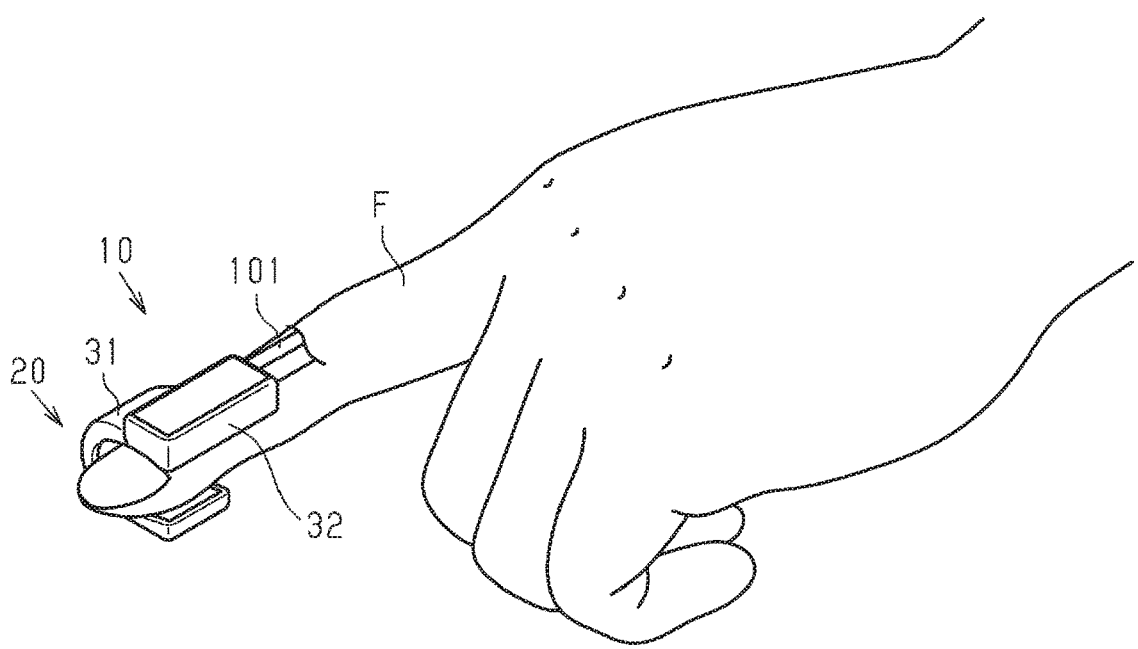
FIG. 3 is a diagram illustrating the pulse oximeter in use.

As shown in FIG. 3, the pulse oximeter 10 is attached to a finger F of a hand of a user when used. When attaching the pulse oximeter 10 to the finger F of the user, the two longitudinal ends of the holder 20 are separated to widen the gap between the two longitudinal ends of the holder 20. Then, the finger F is inserted into the gap between the two longitudinal ends of the holder 20. After inserting the finger F into the curved holder 20, the gap between the two longitudinal ends of the holder 20 is no longer widened. When the gap between the two longitudinal ends of the holder 20 is no longer widened, the reinforcement 80 acts to return to the curved form of the reinforcement 80 prior to the widening and narrowing of the gap between the two longitudinal ends of the holder 20. Consequently, the curved inner surface of the holder 20 comes into close contact with the finger F of the hand of the user. The double-dashed lines in FIG. 2 hypothetically show the finger F.

Blood oxygen saturation level is a value indicating the percentage of hemoglobin that is bonded with oxygen in the red blood cells flowing through the artery. When hemoglobin is bonded with a large amount of oxygen, hemoglobin has a red color under visible light. When hemoglobin is not bonded with a large amount of oxygen, hemoglobin has a blackish color under visible light.

Thus, when a large amount of oxygen is bonded with hemoglobin, in the light emitted from the light emitter 60, the percentage of red light that is transmitted is large. This increases the amount of red light received by the light receiver 70. In contrast, when a large amount of oxygen is not bonded with hemoglobin, in the light emitted from the light emitter 60, the percentage of red light that is transmitted is small. This decreases the amount of red light received by the light receiver 70. In the light emitted from the light emitter 60, the percentage of infrared light that is transmitted through the finger F is constant regardless of the amount of oxygen bonded with hemoglobin. Thus, the amount of infrared light received by the light receiver 70 is not changed by the amount of oxygen bonded with hemoglobin.

The measurement device 103, which is connected to the pulse oximeter 10, calculates the blood oxygen saturation level from the ratio of the amount of infrared light received by the light receiver 70 and the amount of red light received by the light receiver 70.

The advantages of the present preferred embodiment will now be described.

(1) In the preferred embodiment described above, the material of the reinforcement 80 has a Young's modulus that is greater than the Young's modulus of the material of each of the outer portion 30 and the inner portion 40 that form the holder 20. Thus, even when a soft material such as silicone rubber is used as the material of the holder 20, the reinforcement 80 acts to appropriately increase the flexural rigidity of the pulse oximeter 10 in its entirety. Accordingly, when the holder 20 is attached to the finger F, the holder 20 is easily kept on the finger F.

(2) In the preferred embodiment described above, the flexible substrate 50 is located between the outer portion 30 and the inner portion 40. That is, the flexible substrate 50 is arranged inside the holder 20. The flexible substrate 50 has a lower flexural rigidity than the holder 20. Thus, when the pulse oximeter 10 is attached to the finger F of the user, the flexible substrate 50 is bent in conformance with the holder 20. The flexible substrate 50 has little effect on the deformation of the holder 20.

(2) In the preferred embodiment described above, the flexible substrate 50 is fixed to the reinforcement 80. Further, the reinforcement 80 has a higher flexural rigidity than the holder 20. Accordingly, the flexible substrate 50 is fixed more stably than when the flexible substrate 50 is directly fixed to the holder 20.

(4) In the preferred embodiment described above, the inner portion 40 has a lower Shore hardness A than the outer portion 30. Thus, while a certain level of rigidity is obtained for the holder 20 in its entirety, a soft material is employed as the material of the inner portion 40, which is the portion that comes into close contact with the finger F. Further, the employment of the soft inner portion 40 allows the inner portion 40 to come into close contact with the finger F and limits the effect of outside light on the light receiver 70. This improves the measurement accuracy of the pulse oximeter 10.

(5) In the preferred embodiment described above, the light emitter 60 and the light receiver 70 are located between the outer portion 30 and the inner portion 40. More specifically, the light emitter 60 and the light receiver 70 are located toward the inner portion 40 from the inner surface of the outer portion 30 and also toward the outer portion 30 from the outer surface of the inner portion 40. Thus, light needs to be transmitted through the inner portion 40 for the light receiver 70 to receive the light emitted from the light emitter 60. With the preferred embodiment described above, the transmittance of the inner portion 40 with respect to the wavelength band of the light emitted from the light emitter 60 is higher than the transmittance of the outer portion 30 with respect to the wavelength band of the light emitted from the light emitter 60. Thus, the light emitted from the light emitter 60 is transmitted more easily through the inner portion 40 than the outer portion 30. This allows the light emitted from the light emitter 60 to reach the light receiver 70. Further, the transmission of the light emitted from light emitter 60 is more limited in the outer portion 30 than the inner portion 40. Thus, natural light or the like from outside the holder 20 is also prevented from reaching the light receiver 70.

(6) In the preferred embodiment described above, the light emitter 60 is surrounded by the emitter light shield wall 91. Further, the light receiver 70 is surrounded by the receiver light shield wall 92. The light shield walls block the light from the light emitter 60 that is diffused in the inner portion 40 and then directed toward the light receiver 70 and does not block the light from the light emitter 60 that straightly enters the light receiver 70.

(7) In the preferred embodiment described above, the light receiver 70 is surrounded by the receiver light shield wall 92. Thus, even when ambient light, such as light from outside the outer portion 30, is directed toward the light receiver 70, the receiver light shield wall 92 blocks such ambient light. This prevents the light receiver 70 from receiving such ambient light.

The above preferred embodiment may be modified as described below. The above preferred embodiment and the modified examples described below can be combined as long as there are no technical contradictions.

In the preferred embodiment described above, the holder 20 may have any shape as long as it is curved to clamp the finger F. For example, the holder 20 may be shaped to have the form of a curved rod.

In the preferred embodiment described above, the holder 20 may be curved by any amount. For example, the holder 20 may extend to be curved by 360 degrees or greater. When curved by 360 degrees or greater, the finger F can be fitted inside the holder 20 by separating the two ends of the holder 20 to form a gap.

In the above preferred embodiment, a wireless communication device may be incorporated inside the pulse oximeter 10, for example, in the retainer 32 of the outer portion 30, to send and receive signals through wireless communication. The measurement device 103, which is connected by wireless communication to the pulse oximeter 10, may be shared by a plurality of pulse oximeters 10. In other words, a plurality of pulse oximeters 10 may be managed by a single measurement device 103.

In the preferred embodiment described above, the reinforcement 80 only needs to have a curved form and is not limited to the form of a band plate in the above preferred embodiment. For example, the reinforcement 80 may be shaped to have the form of a curved rod.

A plurality of reinforcements 80 may be disposed inside the holder 20. As long as the reinforcement 80 is plate-shaped, an appropriately high flexural rigidity can be obtained for the holder 20 by enlarging the cross-sectional area without overly increasing the thickness of the holder 20.

In the preferred embodiment described above, the material of the reinforcement 80 is not limited to the example of the preferred embodiment. The material of the reinforcement 80 only needs to have a Young's modulus that is greater than the Young's modulus of the holder 20. For example, the material of the reinforcement 80 may be a resin having a greater Young's modulus than the material of the holder 20 or may be a metal such as aluminum.

In the preferred embodiment described above, the material of the outer portion 30 is not limited to the example of the preferred embodiment. For example, the material of the outer portion 30 may be a material of which the Shore A hardness is lower than or equal to that of the inner portion 40. Preferably, the outer portion 30 is formed from rubber because when the pulse oximeter 10 is attached to the finger F of the user, the outer portion 30 comes into contact with the user or a person who is attaching the pulse oximeter 10 to the user. The material of at least the outer portion 30 only needs to have a Young's modulus that is smaller than the Young's modulus of the reinforcement 80.

In the preferred embodiment described above, the hardness of the outer portion 30 and the hardness of the inner portion 40 are not limited to Shore A hardness. For example, Shore D hardness or Vickers hardness may be used, and at least only the inner portion 40 needs to be softer than the outer portion 30.

In the preferred embodiment described above, the material of the inner portion 40 is not limited to the example of the preferred embodiment. For example, the material of the inner portion 40 may be a material of which the Shore A hardness is higher than or equal to that of the outer portion 30. Preferably, the inner portion 40 is formed from rubber because the inner portion 40 directly comes into contact with the finger F of the user. The material of at least the inner portion 40 only needs to have a Young's modulus that is lower than the Young's modulus of the reinforcement 80.

The material of the inner portion 40 does not need to have a lower flexural rigidity than the holder 20 in its entirety. For example, the flexural rigidity of the flexible substrate 50 between the light emitter 60 and the light receiver 70 in the longitudinal direction of the holder 20 only needs to be lower at the portion including the outer portion body 31 than the portion where the cross-sectional area is the smallest in the direction orthogonal to the longitudinal direction of the holder 20. Further, the flexural rigidity of the flexible substrate 50 may be higher than the flexural rigidity of the holder 20. Even in this case, the arrangement of the reinforcement 80 inside the holder 20 returns the deformed reinforcement 80 to its original form. This improves the holding force of the holder 20.

In the preferred embodiment described above, the flexible substrate 50 may be omitted. For example, the light receiver 70 may be connected to a cable separate from the cable group 101, and the separate cable may be connected to the measurement device 103. In this case, since there is no need for cables to be bundled into the cable group 101, the flexible substrate 50 can be omitted.

In the preferred embodiment described above, the transmittance of the outer portion 30 and the transmittance of the inner portion 40 are not limited to the example of the preferred embodiment. For example, as long as the inner portion 40 includes holes in the thickness-wise direction of the holder 20 at positions aligned with the light emitter 60 and the light receiver 70, the light emitted from the light emitter 60 can pass through the corresponding hole and be transmitted through the finger F. Further, the light transmitted through the finger F can pass through the hole at the side of the light receiver 70 and be received by the light receiver 70. Thus, for example, the inner portion 40 does not have to transmit the light emitted from the light emitter 60.

The inner portion 40 does not have to be entirely colorless and transparent. The inner portion 40 may be colorless and transparent at only locations corresponding to the light emitter 60 and the light receiver 70, and the other portions may be colored in black under visible light. In this case, the light emitted from the light emitter 60 is transmitted through the inner portion 40 and received by the light receiver 70 in the same manner as when there are holes as described above.

In the preferred embodiment described above, the emitter light shield wall 91 does not need to be shaped as a quadrangular frame like in the above preferred embodiment. The emitter light shield wall 91 only needs to be disposed in the range where light has to be blocked. For example, a portion at a first longitudinal end side of the holder 20 may be omitted. The same applies to the receiver light shield wall 92.

In the preferred embodiment described above, the emitter light shield wall 91 may be omitted. For example, if the light emitter 60 has high directivity, the emitter light shield wall 91 can be omitted as long as the inner portion 40 impedes the transmission of light from the light emitter 60 that does not pass through the finger F.

In the preferred embodiment described above, the receiver light shield wall 92 may be omitted. For example, if the light receiver 70 has high directivity, the receiver light shield wall 92 can be omitted as long as the light receiver 70 does not receive the light that is not transmitted through the finger F but is transmitted through the inner portion 40.

In the preferred embodiment described above, the pulse oximeter 10 can measure the pulse instead of or in addition to the blood oxygen saturation level. When comparing the amount of red light and infrared light received by the light receiver 70 as described above, fluctuations in the amount of light received by the light receiver 70 can be measured to measure the pulse.

In the preferred embodiment described above, the holder 20 holds the finger F from beside the finger F. However, the holder 20 may hold the finger F from the tip of the finger F.

The set of the light emitter 60 and the light receiver 70 in the preferred embodiment may be referred to as an optical physiological sensor including a light emitting element and a light receiving element. The holder 20 of the preferred embodiment may be referred to as a C-shaped elastic probe or hingeless elastic probe that accommodates the light emitter 60 and the light receiver 70 and is configured to be elastically attached to the periphery (e.g., finger F) of a measured subject to position the light emitter 60 and the light receiver 70 at different locations on the surface (skin) of the periphery of the measured subject. The outer portion 30 and the inner portion 40 of the preferred embodiment may collectively be referred to as the skin layer, and the outer portion 30 and the inner portion 40 may respectively be referred to as the outer skin layer and the inner skin layer. One or both of the outer portion 30 and the inner portion 40 may be partially or entirely formed from an electrical insulating cushion material. The flexible substrate 50 of the preferred embodiment may be referred to as a circuit substrate that is electrically connected to the optical physiological sensor (60, 70). The reinforcement 80 of the preferred embodiment may be referred to as a curved core layer or a curved plate reinforcement core including a length, a thickness, a first position (emitter receptacle 81) corresponding to the light emitter 60, a second position (receiver receptacle 82) corresponding to the light receiver 70 and separated from the first position in the longitudinal direction of the reinforcement 80, and a curved middle portion located between the first position and the second position.

According to preferred embodiment 1, a pulse oximeter (10) includes:

an optical physiological sensor (60, 70) including a light emitting element and a light receiving element; and a C-shaped elastic probe (20) that accommodates the optical physiological sensor (60, 70) and is configured to be elastically attached to a periphery of a measured subject to position the light emitting element and the light receiving element at different locations on a surface of the periphery of the measured subject, wherein the C-shaped elastic probe (20) includes a skin layer (30, 40) and a curved core layer (80) that is surrounded by the skin layer (30, 40) or embedded inside the skin layer (30, 40), the skin layer (30, 40) has a first Young's modulus, and the curved core layer (80) has a second Young's modulus that is greater than the first Young's modulus.

According to preferred embodiment 2, the skin layer (30, 40) includes:

an inner skin layer (40) including a radially inward surface, which may be a concave surface, facing toward the surface of the periphery of the measured subject when the C-shaped elastic probe (20) is attached to the periphery of the measured subject, an outer skin surface (30) including a radially outward surface, which may be a convex surface and is opposite the radially inward surface, and the curved core layer (80) is located between the inner skin layer (40) and the outer skin layer (30).

According to preferred embodiment 3, the probe (20) includes a circuit substrate (50) that differs from the curved core layer (80), wherein the circuit substrate (50) is electrically connected to the optical physiological sensor and adhered or fixed to the core layer (80).

According to preferred embodiment 4, the core layer (80) includes a radially inward surface, which may be a concave surface, and a radially outward surface, which may be a convex surface, and the circuit substrate (50) is in close contact with the radially outward surface of the core layer (80).

According to preferred embodiment 5, the inner skin layer (40) has a first Shore hardness, and the outer skin layer (30) has a second Shore hardness, and the first Shore hardness of the inner skin layer (40) is lower than the second Shore hardness of the outer skin layer (30).

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A pulse oximeter comprising:
    a holder including a curved shape;
    a light emitter coupled to the holder to emit light inwardly from the holder;
    a light receiver coupled to the holder at a position opposed to the light emitter to receive the light emitted from the light emitter; and
    a reinforcement inside the holder that extends from the light emitter to the light receiver in conformance with the curved shape of the holder, wherein
    a material of the reinforcement has a Young's modulus that is greater than a Young's modulus of a material of the holder.

2. The pulse oximeter according to claim 1, further comprising a plate-shaped substrate inside the holder and electrically connected to the light emitter and the light receiver, wherein
    the plate-shaped substrate
    has a lower flexural rigidity than a portion of the holder between the light emitter and the light receiver where a cross-sectional area orthogonal to an extending direction of the holder extending from the light emitter to the light receiver is smallest.

3. The pulse oximeter according to claim 2, wherein the plate-shaped substrate extends along the reinforcement and is fixed to the reinforcement.

4. The pulse oximeter according to claim 1, wherein
    the holder includes an inner portion located at an inner side of the holder and an outer portion located at an outer side of the holder from the inner portion, and
    the inner portion has a lower hardness than the outer portion.

5. The pulse oximeter according to claim 1, wherein
    the holder includes an inner portion located at an inner side of the holder and an outer portion located at an outer side of the holder from the inner portion,
    the light emitter and the light receiver are located between an inner surface of the outer portion and an outer surface of the inner portion, and
    the inner portion has a higher transmittance than the outer portion with respect to a wavelength band of the light emitted from the light emitter.

6. The pulse oximeter according to claim 5, further comprising an emitter light shield wall and a receiver light shield wall inside the holder, wherein
    the emitter light shield wall surrounds the light emitter in a view of the light emitter taken from the light receiver, and
    the receiver light shield wall surrounds the light receiver in a view of the light receiver taken from the light emitter.

* * * * *